United States Patent
Yamamoto et al.

(10) Patent No.: US 9,835,704 B2
(45) Date of Patent: Dec. 5, 2017

(54) HEAT EMISSION DISTRIBUTION INFORMATION GENERATING DEVICE AND METHOD, MAGNETIC RESONANCE IMAGING DEVICE, AND PROGRAM

(71) Applicant: NATIONAL UNIVERSITY CORPORATION HOKKAIDO UNIVERSITY, Sapporo-shi, Hokkaido (JP)

(72) Inventors: Toru Yamamoto, Sapporo (JP); Yuta Kobayashi, Sapporo (JP)

(73) Assignee: National University Corporation Hokkaido, Hokkaido (JP)

( * ) Notice: Subject to any disclaimer, the term of this patent is extended or adjusted under 35 U.S.C. 154(b) by 508 days.

(21) Appl. No.: 14/389,313

(22) PCT Filed: Mar. 30, 2013

(86) PCT No.: PCT/JP2013/059784
§ 371 (c)(1),
(2) Date: Sep. 29, 2014

(87) PCT Pub. No.: WO2013/147281
PCT Pub. Date: Oct. 3, 2013

(65) Prior Publication Data
US 2015/0331075 A1    Nov. 19, 2015

(30) Foreign Application Priority Data

Mar. 30, 2012 (JP) .................................. 2012-080885

(51) Int. Cl.
*G01V 3/00* (2006.01)
*G01R 33/48* (2006.01)
(Continued)

(52) U.S. Cl.
CPC .......... *G01R 33/4804* (2013.01); *A61B 5/055* (2013.01); *G01R 33/288* (2013.01)

(58) Field of Classification Search
CPC .............. G01R 33/543; G01R 33/5659; G01R 33/3415; G01R 33/36; A61B 5/055
(Continued)

(56) References Cited

U.S. PATENT DOCUMENTS 5,916,161 A * 6/1999 Ishihara ................. A61B 5/055
324/315
2010/0090695 A1* 4/2010 Kassai ............. G01R 33/56518
324/309

(Continued)

FOREIGN PATENT DOCUMENTS

JP      2009-160215      7/2009

OTHER PUBLICATIONS

Translation of Kumai (JP 2009160215 A) listed in the IDS, publication date: Jul. 23, 2009.*

(Continued)

*Primary Examiner* — Walter L Lindsay, Jr.
*Assistant Examiner* — Frederick Wenderoth
(74) *Attorney, Agent, or Firm* — K&L Gates LLP; Louis C. Cullman; Michelle Glasky Bergman

(57) ABSTRACT

In an image creating device, an obtainer obtains the phase of a magnetic resonance signal generated from a target object upon application of a static magnetic field and a high-frequency magnetic field to the target object (step S102). A calculator calculates a change level of the obtained phase per a predetermined distance in a direction of the static magnetic field (step S103). A generator generates an image representing a positional distribution of a parameter depending on the calculated change level (step S106).

11 Claims, 10 Drawing Sheets

(51) Int. Cl.
*A61B 5/055* (2006.01)
*G01R 33/28* (2006.01)

(58) Field of Classification Search
USPC .......................................................... 324/309
See application file for complete search history.

(56) References Cited

U.S. PATENT DOCUMENTS

2010/0237861 A1* 9/2010 Hennel ................ G01R 33/246
324/307
2011/0159371 A1* 6/2011 Lyden .................... A61N 1/375
429/231.95

OTHER PUBLICATIONS

Hand, Jeffrey W., et al., "Electromagnetic and Thermal Modeling of SAR and Temperature Fields in Tissue Due to an RF Decoupling Coil", Magnetic Resonance in Medicine, 42:183-192 (1999).

Ehses, Philipp et al., "MRI Thermometry: Fas Mapping of RF-Induced Heating Along Conductive Wire", Magnetic Resonance in Medicine, 60:457-461 (2008).

Katscher, Ulrich et al., "Determination of Electric Conductivity and Local SAR Via B1 Mapping", IEEE Transactions on Medical Imaging, 28(9):365-1374, Sep. 2009.

Chang-Sheng, Mei et al., "Ultrafast 1D MR thermometry using phase or frequency mapping", Magnetic Resonance Materials in Physics, Biology and Medicine, Chapman and Hall, London GB 2011, vol. 25, No. 1, pp. 5-14.

Rieke, V et al., "MR thermometry", Journal of Magnetic Resonance Imaging, Society for Magnetic Resonance Imaging, Oak Brook, IL, US 2008, vol. 27, pp. 376-390.

Voigt, T., et al., "Patient-specific in vivo local SAR Estimation and Validation", Proceedings of the 18th Joint Annual Meeting of the ISMRM and ESMRMB, 2010, pp. 3876.

Extended European Search Report dated Apr. 2, 2015.

* cited by examiner

- COPPER-WIRE COIL 430
- PAPER DISH 410
- WRAP 420
- EGG ALBUMEN 400
- CONTACT

- COPPER-WIRE COIL 430
- CONTACT
- EGG ALBUMEN 400
- WRAP 420
- PAPER DISH 410

PAPER DISH 410

HEAT EMISSION DISTRIBUTION INFORMATION GENERATING DEVICE AND METHOD, MAGNETIC RESONANCE IMAGING DEVICE, AND PROGRAM

TECHNICAL FIELD

The present disclosure relates to a device and a method that generate heat emission distribution information, a magnetic resonance imaging device, and a program.

BACKGROUND ART

Magnetic resonance imaging (MRI: Magnetic Resonance Imaging) technologies are known which image the inside of a target object using nuclear magnetic resonance. The MRI technologies are widely utilized, having capability for imaging a tissue of a target object non-invasively, and excellent resolution performance for, in particular, soft tissues, such as brain and muscles. In addition, the higher the intensity of an applied magnetic field is, the finer the obtained image becomes, thus the magnetic field of such technologies is becoming stronger.

An MRI device applies a magnetic field that varies at a high frequency (Radio Frequency) to a target object. Hence, a current induced by a variable magnetic field may be generated. When an induced current is generated, the precision of the image decreases, and it may be heated due to the Joule heat. As to such heat generation by an induced current, for example, Non-patent Literature 1 discloses a technology of obtaining a distribution of generated heat from the intensity distribution of a magnetic field through a method utilizing the MRI technology.

CITATION LIST

Non Patent Literature

Non-patent Literature 1: U. Katscher, T. Voigt, C. Findeklee, P. Vernickel, K. Nehrke, O. Dossel, IEEE Transactions on Medical Imaging, Vol. 28, No. 9, pp. 1365-1374, 2009

SUMMARY OF INVENTION

Technical Problem

In order to obtain a distribution of generated heat through the technology disclosed in Non-patent Literature 1, it is necessary to increase the intensity of the high-frequency magnetic field up to a level at which an image of a target object is actually obtained through the MRI. As a result, it is difficult to obtain the distribution of heat generation quantities before a highly precise magnetic resonance image of a target object is actually obtained. In addition, a scheme of largely changing the hardware resources of an MRI device to find a heat emission location has been proposed, but it is difficult to apply such a scheme to a clinical MRI. Therefore, a device, a method, and the like which are applicable to a clinical MRI and which predict a heat generation quantity and a distribution thereof without applying a highly intensive high-frequency magnetic field to a target object are demanded.

The present disclosure has been made in order to address the aforementioned problems, and it is an objective of the present disclosure to provide a device, a method, and a program which are suitable for predicting amount of to-be generated heat originating from an application of a high-frequency magnetic field.

Solution to Problem

To accomplish the above objective, a device according to a first aspect of the present disclosure generates information representing a heat generation distribution, and the device includes:

an obtainer that obtains a phase of a magnetic resonance signal generated from a target object upon application of a static magnetic field and a high-frequency magnetic field to the target object;

a calculator that calculates a change level of the obtained phase per a predetermined distance in a direction of the static magnetic field; and a generator that generates information representing a positional distribution of a parameter depending on the calculated change level.

The parameter is, for example, proportional to a square of the calculated change level.

For example, the calculator further calculates a change level of the obtained phase per a predetermined distance in a direction orthogonal to the direction of the static magnetic field, and the generator generates information representing a positional distribution of a parameter, the parameter being obtained by an addition of a square of the calculated change level in the direction of the static magnetic field and a square of the calculated change level in the orthogonal direction to the direction of the static magnetic field at a predetermined ratio.

For example, the calculator further calculates change levels of the obtained phase per a predetermined distance in two directions orthogonal to the direction of the static magnetic field and intersecting with each other at right angle, and the generator creates an image representing a positional distribution of a parameter, the parameter being obtained by an addition of a square of the calculated change level in the direction of the static magnetic field, and, a square of a sum of the calculated change levels in the two directions orthogonal to the direction of the static magnetic field and intersecting with each other at right angle at a rate of substantially 2:1.

An intensity of the high-frequency magnetic field is, for example, lower than an intensity of a high-frequency magnetic field to be applied to the target object during a time period of magnetic resonance image-capture being performed on the target object. The intensity of the high-frequency magnetic field is, for example, lower than 1/20 of the intensity of the high-frequency magnetic field to be applied to the target object during a time period of magnetic resonance image-capture being performed on the target object.

Image information representing amount of to-be-generated heat predicted may be formed from the positional distribution of the parameters.

The device may further include a warner that outputs a warning when a heat generation quantity predicted based on the positional distribution exceeds a predetermined allowable level.

The device may further include a setter that determines an image-capture condition to be set during a time period of magnetic resonance image-capture being performed on the target object so as to prevent, when a heat generation quantity predicted based on the positional distribution exceeds a predetermined allowable level, the heat generation quantity from exceeding the allowable level.

To accomplish the above objective, a magnetic resonance imaging device according to a second aspect of the present disclosure includes the aforementioned device.

To accomplish the above objective, a method according to a third aspect of the present disclosure includes:

an obtaining step for obtaining a phase of a magnetic resonance signal generated from a target object upon application of a static magnetic field and a high-frequency magnetic field to the target object;

a calculating step for calculating a change level of the obtained phase per a predetermined distance in a direction of the static magnetic field; and a generating step for generating information representing a parameter depending on the calculated change level.

To accomplish the above objective, a program according to a fourth aspect of the present disclosure causes a computer to function as:

an obtainer that obtains a phase of a magnetic resonance signal generated from a target object upon application of a static magnetic field and a high-frequency magnetic field to the target object;

a calculator that calculates a change level of the obtained phase per a predetermined distance in a direction of the static magnetic field; and a generator that generates information representing a parameter depending on the calculated change level.

Advantageous Effects of Invention

According to the present disclosure, it becomes possible to obtain information for obtaining a predicted distribution of heat generation quantities originating from an application of a high-frequency magnetic field.

DESCRIPTION OF EMBODIMENTS

An embodiment of the present disclosure will be explained with reference to the accompanying drawings.

An image creating device of this embodiment generates information indicating a distribution of phase change (change in phase) of a magnetic resonance signal (MR signal) to predict the distribution of heat to-be generated by an induced current in a method of imaging the inside of a target object through magnetic resonance imaging (MRI: Magnetic Resonance Imaging). The information be of any form, but in this embodiment, this information is image information representing the distribution of phase change in an MR signal. In addition, as will be discussed later, this phase change corresponds to a heat generation quantity at the location thereof.

Figure 1:
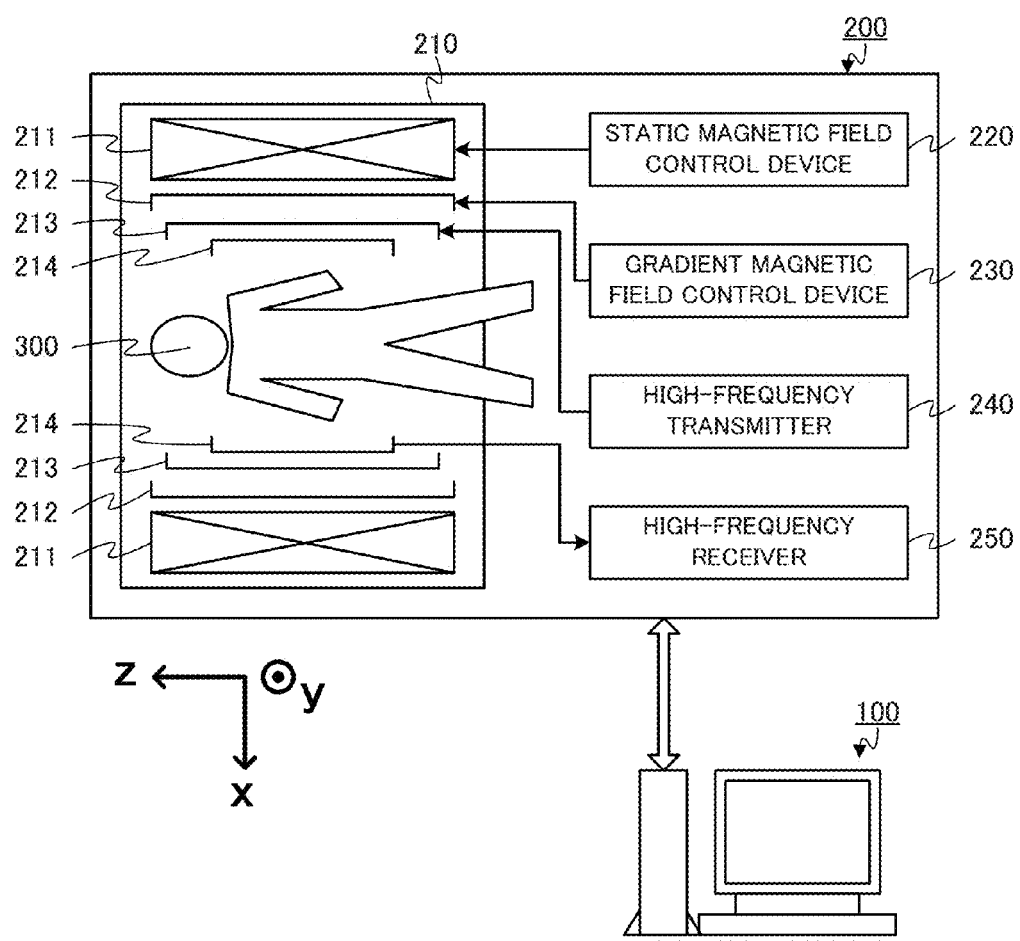
FIG. 1 is a diagram for explaining an outline of an MRI device with which an image creating device according to an embodiment of the present disclosure is used.

FIG. 1 is a diagram for explaining an outline of an MRI device with which the image creating device according to the embodiment of the present disclosure is used. An MRI device 200 of this embodiment is capable of creating an image representing the interior of a target object through a conventionally well-known scheme. The major configuration of the MRI device 200 will be briefly explained below.

The MRI device 200 includes a gantry 210, a static magnetic field control device 220, a gradient magnetic field control device 230, a high-frequency (radio-frequency) transmitter 240, a high-frequency receiver 250, or the like.

Placed within the gantry 210 is a living body 300 that is an example target object. Also, disposed in the gantry 210 are a static magnetic field magnet 211, a gradient magnetic field coil 212, a transmitter coil 213, and a receiver coil 214 so as to surround the circumference of the target object.

In the following explanation, it is presumed that the MRI device 200 is a typical horizontal MRI device, the direction of the static magnetic field, that is, the direction in which the target object is inserted in the gantry 210 is defined as a z direction, the direction in a horizontal plane orthogonal to the z direction is defined as an x direction, and the vertical direction is defined as a y direction. However, the MRI device 200 of the present disclosure is not limited to the horizontal MRI device, and may be other type like a vertical MRI device. When, for example, the MRI device 200 is a vertical MRI device, the coordinate axes are defined in such a way that the z direction that is the direction of a static magnetic field becomes the vertical direction and the x direction and the y direction become directions within a horizontal plane. In this case, the vertical MRI device can be likewise explained when the MRI device 200 is a horizontal MRI device.

The static magnetic field control device 220 controls the static magnetic field magnet 211, generates a uniform magnetic field in the gantry 210, and gives an orientation to nucleus spins in the target object. The static magnetic field magnet 211 includes, for example, a shim coil including an electromagnetic coil or a multi-channel electric magnet, and generates a uniform static magnetic field in the z direction in the gantry 210 under a control of an appropriate cooling device and a constant-temperature device. The static magnetic field generated in the z direction coordinates the directions of hydrogen nucleus spins in the target object in the z direction. The static magnetic field magnet 211 may be a permanent magnet, or may be a normal conduction magnet or superconductive magnet.

The gradient magnetic field control device 230 controls the gradient magnetic field coil 212 to generates a gradient magnetic field which has a gradient intensity in the gantry 210. More specifically, the gradient magnetic field coil 212 includes three sets of coils that generate gradient magnetic fields in the x, y, and z directions, respectively, so as to obtain three-dimensional positional information. The intensity of the applied magnetic field is changed in accordance with the position in the gantry 210, thereby changing the frequency and a phase of precession movement in accordance with the position. Hence, positional information is added to a signal obtained from the hydrogen nucleus in the target object.

The high-frequency transmitter 240 controls the transmitter coil 213, and applies high-frequency (RF: Radio Frequency) pulses to the target object, thereby generating a high-frequency magnetic field. Such RF pulses are applied so as to rotate within a vertical plane (xy plane) orthogonal to a direction in which the static magnetic field is applied. When RF pulses rotating at a frequency resonant to a nucleus in precession movement are applied, the nucleus is excited, and the phase of the precession movement is also aligned. Conversely, when an application of RF pulses is terminated, the excited nucleus returns to a steady condition.

The high-frequency receiver 250 controls the receiver coil 214, and receives a magnetic resonance signal (MR signal) produced through a relaxation process of the excited nucleus in the target object to a steady condition. The high-frequency receiver 250 includes appropriate amplifier, filter, analog/digital converter, or the like, and converts the received MR signal into data that can be digitalized. The converted data is transmitted to a general-purpose computer, and is subjected to image processing like Fourier transform, thus an image representing the inside of the target object is created.

According to the MRI device 200, a magnetic field that changes over time, such as a high-frequency magnetic field, is applied, and thus an induced current is generated based on the Faraday's law of electromagnetic induction. The induced current becomes an eddy current and intensively flows when a loop circuit is accidentally formed in a part of the living body 300, the surrounding metal cable, or the like. When an eddy current is generated, the magnetic field induced by such a current decreases the image-capture precision of an MR signal, and also heat may be generated by Joule heat thereof, which is not suitable. The image creating device 100 of this embodiment focuses on the phase information of the MR signal, and generates image information representing the positional distribution thereof to predict a heat generation quantity by an eddy current.

The image creating device 100 is connected to the MRI device 200, obtains data of the MR signal received by the high-frequency receiver 250, and creates an image representing the positional distribution of parameters including the phase change level of the MR signal.

Figure 2:
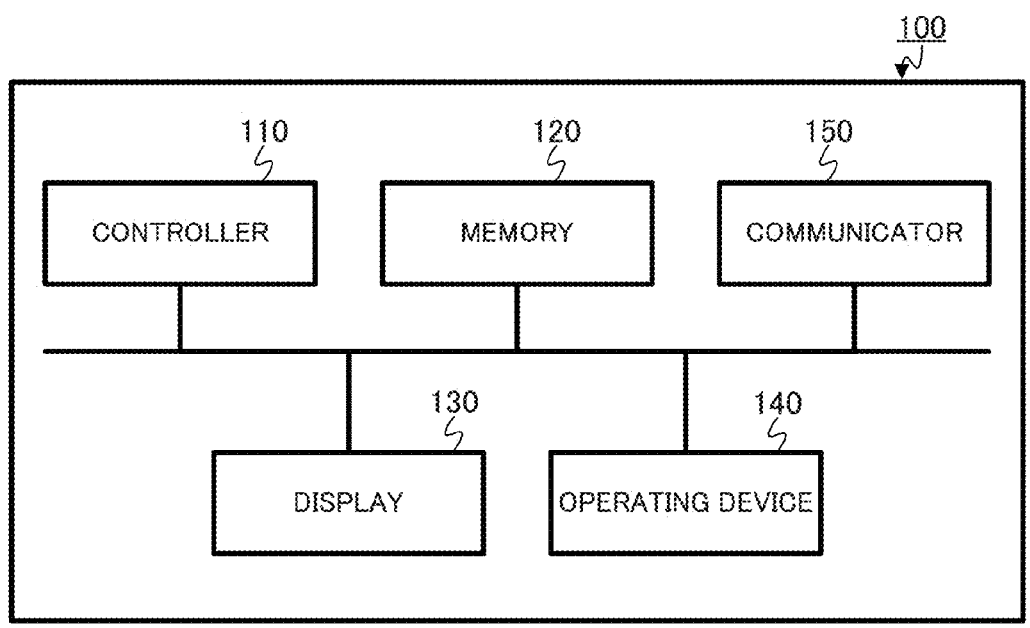
FIG. 2 is a block diagram illustrating an example general configuration of the image creating device.

FIG. 2 is a block diagram illustrating an example general configuration of the image creating device 100. The image creating device 100 includes a controller 110, a memory 120, a display 130, an operating device 140, and a communicator 150. Those components are mutually connected via a bus.

The controller 110 includes a CPU (Central Processing Unit), a ROM (Read Only Memory), a RAM (Random Access Memory), and so on. In the controller 110, the CPU utilizes the RAM as a work memory to appropriately execute various programs stored in the ROM and the memory, thereby controlling the operation of each component of the image creating device 100.

The memory 120 is, for example, a non-volatile memory like a hard disk or a flash memory. The memory 120 stores various data necessary for an image creating process.

The display 130 includes, for example, a CRT (Cathode Ray Tube) or an LCD (Liquid Crystal Display). The display 130 displays various images, such as an image created by the image creating device 100 and an image for allowing an operator to operate the image creating device 100, under the control of the controller 110.

The operating device 140 includes, for example, a keyboard and a mouse. The operator operates the operating device 140 to enter various operation instructions like an instruction to obtain image information from the MRI device 200.

The communicator 150 is an appropriate communication device to be connected with the exterior of the image creating device 100. The communicator 150 is connected with the MRI device 200, and exchanges data with the MRI device 200 under the control of the controller 110. In addition, the communicator 150 may be connected to a network through an appropriate modulator/demodulator device and the like, and exchange data with other computers.

The configuration of such an image creating device 100 is not limited to an external connection with the MRI device 200, but may be a built into the interior of the MRI device 200. That is, the image creating device 100 may be included in the MRI device 200. In addition, the image creating device 100 may be the same as an image processing computer utilized in a normal MRI examination.

An explanation will now be given of a phase change in the MR signal utilized by the image creating device 100 of this embodiment for image creation with reference to FIGS. 3 to 5.

Figure 3:
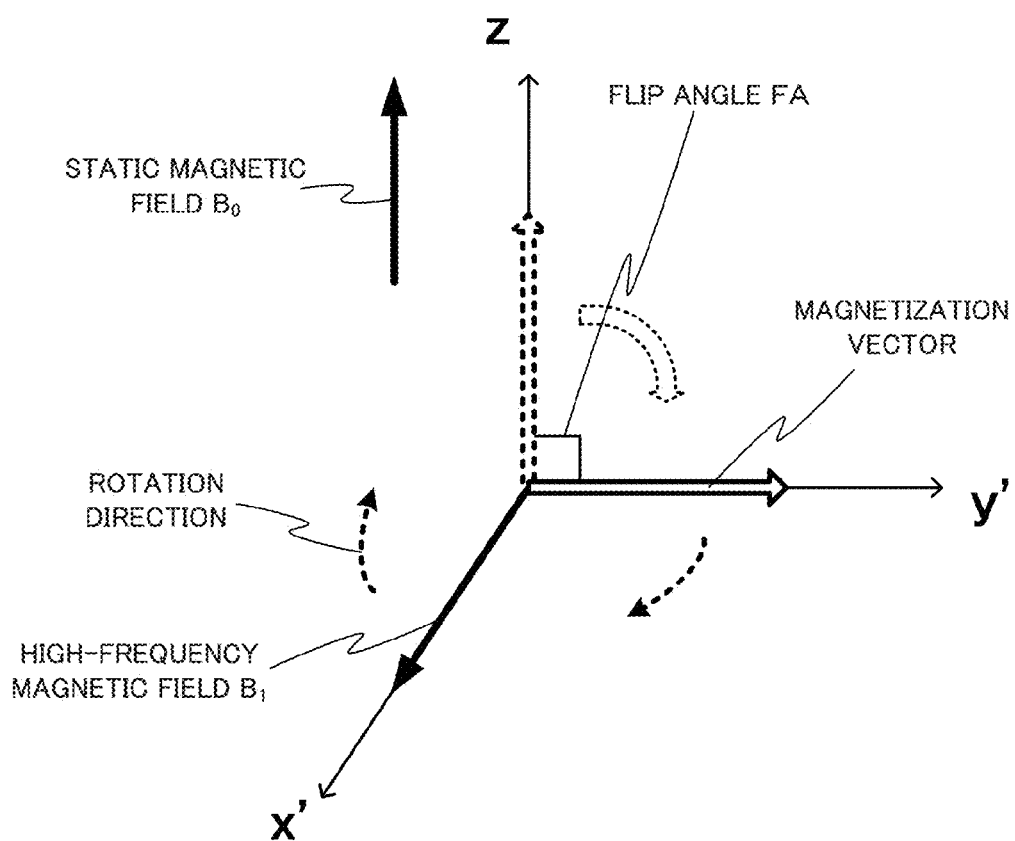
FIG. 3 is a diagram illustrating how a magnetization vector changes direction along with an application of a high-frequency magnetic field.

FIG. 3 is a diagram illustrating how the direction of a magnetization vector changes along with an application of RF pulses. In FIG. 3, an explanation will be given with a rotational coordinates x', y' in which a high-frequency magnetic field $B_1$ is directed to just an x' direction and stands still by RF pulses applied so as to rotate within the xy plane.

In this case, the term magnetization vector is a synthesis vector of nucleus spins in the target object. When no RF pulse is applied, respective nuclei have independent precession movements with the direction of a static magnetic field $B_0$ serving as an axis. Hence, the magnetization vector that is a synthesis vector thereof is directed to the direction of the static magnetic field $B_0$ (z direction). Conversely, when RF pulses are applied and a high-frequency magnetic field $B_1$ is applied, some nuclei are excited and the phases of the precession movements are aligned. Hence, the magnetization vector flips in the direction out of the direction of the static magnetic field $B_0$. As illustrated in FIG. 3, the magnetization vector changes the direction thereof so as to fall down in the y' direction by the high-frequency magnetic field $B_1$ in the x' direction.

The angle changed at this time, that is, an angle between the direction of the magnetization vector and the direction of the static magnetic field $B_0$ (z direction) is referred to as a flip angle (FA: Flip Angle). In general, the FA takes a value between 0 to 180 degrees, and is an angle with a magnitude in proportional to the intensity of the high-frequency magnetic field $B_1$. In order to facilitate understanding, in the example case in FIG. 3, a condition in which the high-frequency magnetic field $B_1$ with an intensity causing the FA to be 90 degrees is applied is illustrated.

Figure 4:
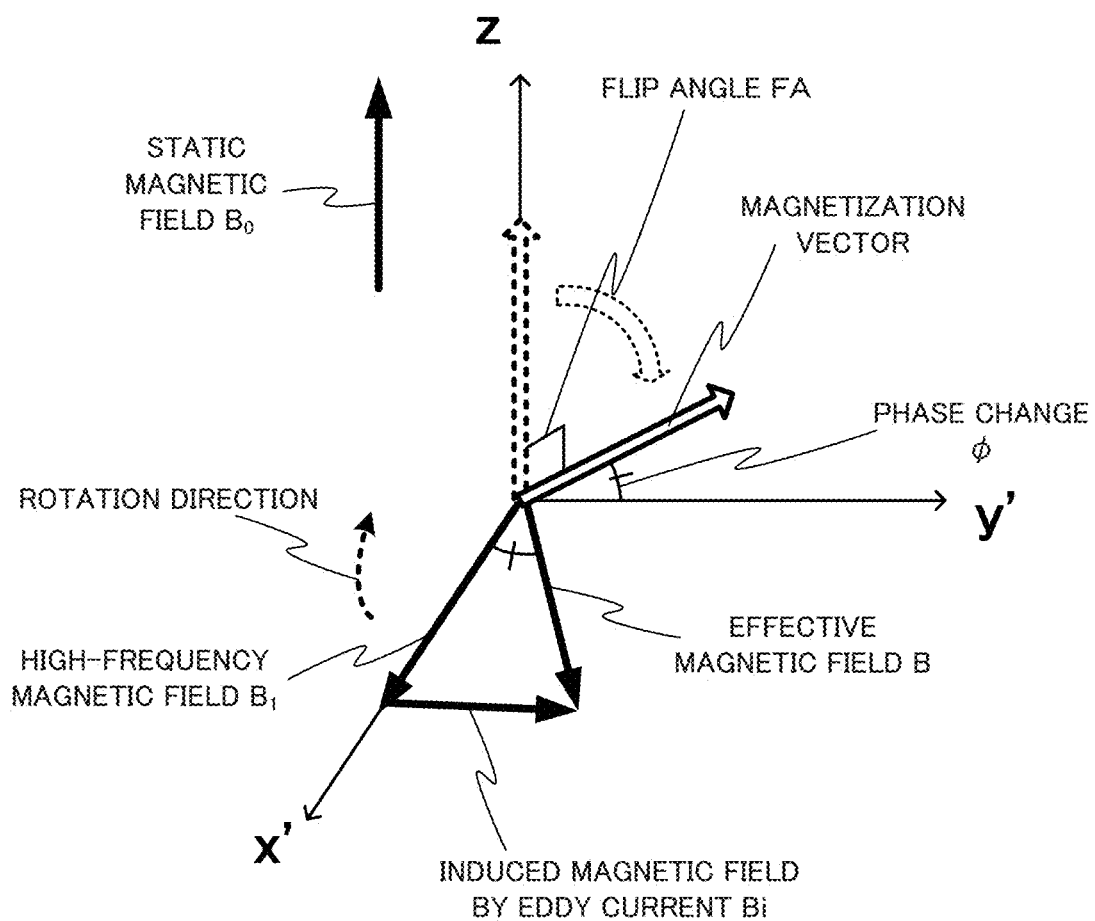
FIG. 4 is a diagram illustrating how a phase of a magnetization vector changes along with a generation of an induced magnetic field.

In contrast, FIG. 4 illustrates how the phase of the magnetization vector changes in accordance with a generation of an induced magnetic field by an eddy current.

When an eddy current is generated, due to the law of electromagnetic induction, a magnetic field is induced in a direction making the change of the rotating high-frequency magnetic field $B_1$ weakened. Hence, an induced magnetic field Bi is generated in an opposite direction to the rotation direction. An effective magnetic field B that is a synthesis of the induced magnetic field $B_i$ with the high-frequency magnetic field $B_1$ has a phase delayed relative to that of the high-frequency magnetic field $B_1$.

When the effective magnetic field having the phase delayed is generated, the phase of the magnetization vector flipped by the effective magnetic field is delayed by the same level. More specifically, as illustrated in FIG. 3, when no induced magnetic field $B_i$ has been generated, the magnetization vector changes the direction as if it falls down from z direction to the y' direction. Conversely, as illustrated in FIG. 4, when the induced magnetic field $B_i$ is generated, the magnetization vector flips in a direction out of the y' direction. A phase change level ϕ from the y' direction becomes the same value as the phase change level of the effective magnetic field B from the high-frequency magnetic field $B_1$.

The level of the phase change of such a magnetization vector is the same when the high-frequency magnetic field $B_1$ with a different intensity is applied. This will be explained in more detail with reference to FIG. 5.

Figure 5:
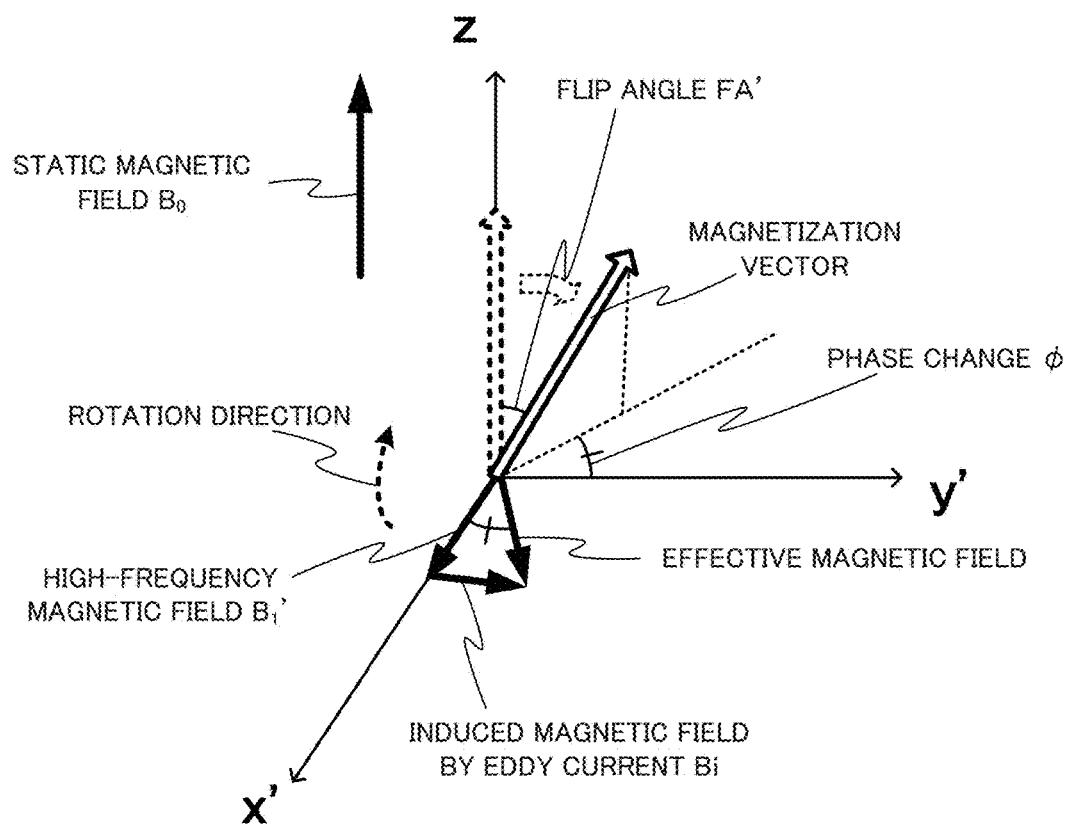
FIG. 5 is another diagram illustrating how a phase of a magnetization vector changes along with a generation of an induced magnetic field.

FIG. 5 illustrates a condition in which a high-frequency magnetic field $B_1$' with a lower intensity than that of the high-frequency magnetic field $B_1$ in FIG. 4 is applied. An angle FA' of the flipping magnetization vector from the z direction reflects the high-frequency magnetic field $B_1$' with a low intensity and becomes smaller than the FA in FIG. 4. Conversely, the intensity of the induced magnetic field $B_i$ by the eddy current is proportional to the intensity of the high-frequency magnetic field $B_1$', and thus the phase change of the effective magnetic field B from the high-frequency magnetic field $B_1$', becomes the same value regardless of the intensity of the high-frequency magnetic field. Hence, the phase change level ϕ of the magnetization vector flipped by the effective magnetic field becomes the same value regardless of the intensity of the high-frequency magnetic field $B_1$'.

The phase of the MR signal output from a nucleus having the phase changed as explained above is also changed, and thus the phase information of the MR signal becomes a barometer for checking a generation of an eddy current. In addition, the phase change level ϕ is independent from the intensity of the high-frequency magnetic field, and thus it is a suitable barometer that enables a prediction of a generation of an eddy current without an application of a high-frequency magnetic field with a high intensity.

In the following explanation, a more quantitative explanation will be given of a relationship between a heat generation quantity SAR (Specific Absorption Rate) by the Joule heat of an eddy current and the phase information of an MR signal.

When the conduction rate of the target object is σ and the electric field vector of the eddy current is $\vec{E}$, the heat generation quantity SAR per a unit mass in the target object caused by an eddy current can be expressed by a formula (1).

[Formula 1]

$$SAR \propto \sigma |\vec{E}|^2 \quad (1)$$

That is, the heat generation quantity SAR per a unit mass is proportional to a value obtained by multiplying the square of the magnitude of the electric field vector $\vec{E}$ by an eddy current by the conduction rate σ.

In this case, when $\vec{B}$ is defined as an effective magnetic field vector that is a sum of the high-frequency magnetic field vector $\vec{B_1}$ and the induced magnetic field vector $\vec{B_i}$, the electric field vector $\vec{E}$ can be expressed as a following formula (2). In this formula, rot is the operator of rotation, μ is the permeability of the target object, ∈ is the dielectric constant of the target object, and ω can be obtained by multiplying the resonant frequency by 2π.

[Formula 2]

$$\vec{E} = \frac{rot\vec{B}}{\mu(\sigma + j\omega\varepsilon)} \quad (2)$$

That is, the magnitude of the electric field vector $\vec{E}$ inducing the eddy current is proportional to the magnitude of rotation |rot$\vec{B}$| of the effective magnetic field vector $\vec{B}$. Hence, based on the formula (1), the SAR is also proportional to the square of |rot$\vec{B}$| as expressed by a formula (3).

[Formula 3]

$$SAR \propto |rot\vec{B}|^2 \quad (3)$$

The effective magnetic field vector $\vec{B}$ can be expressed as a formula (4) based on the Stoke's theorem.

[Formula 4]

$$\int_s rot\vec{B} \cdot d\vec{s} = \oint_l \vec{B} \cdot d\vec{l} \quad (4)$$

In this case, when the integral area is taken in a minute area ds=dz·dx in the zx plane, the left side of the formula (4) can be expressed as a formula (5) which is a formula relating to the y component of rot$\vec{B}$.

[Formula 5]

$$(rot\vec{B})_y \cdot dz \cdot dx \quad (5)$$

In addition, the direction of the high-frequency magnetic field vector $\vec{B_1}$ is substantially perpendicular to the direction of the static magnetic field vector $\vec{B_0}$. In consideration of this fact, the effective magnetic field vector $\vec{B}$ can be deemed as having no z direction (direction of static magnetic field vector $\vec{B_0}$) component. Hence, the right side of the formula (4) can be expressed as a formula (6).

[Formula 6]

$$\left(\overrightarrow{B_{(z+dz)}} - \overrightarrow{B_{(z)}}\right) \cdot \vec{dx} = \frac{\partial \vec{B}_{(z)}}{\partial z} dz \cdot \vec{dx} \quad (6)$$

Since the formula (5) and the formula (6) are equal, the following formula (7) can be obtained.

[Formula 7]

$$\left(rot\vec{B}\right)_y = \left(\frac{\partial B}{\partial z}\right)_x \quad (7)$$

In the stationary coordinate system, the effective magnetic field vector B' can be defined as a formula (8). In this case, t is a time.

[Formula 8]

$$\vec{B} = [B\sin(\omega t - \phi), B\cos(\omega t - \phi)] \quad (8)$$

When the formula (8) is applied, the right side of the formula (7) can be expressed as a formula (9).

[Formula 9]

$$(rot\vec{B})_y = \left(\frac{\partial B}{\partial z}\right)_x = -B\cos(\omega t - \phi) \cdot (\nabla \phi)_z + (\nabla B)_z \sin(\omega t - \phi) \quad (9)$$

A change in the effective magnetic field vector $\vec{B}$ in the z direction is mainly a change in phase, and a change in intensity is relatively small. That is, a formula (11) is satisfied. Hence, the second term in the rightmost side of the formula (9) is ignorable, and the formula (9) can be converted into the formula (10).

[Formula 10]

$$(rot\vec{B})_y = \left(\frac{\partial B}{\partial z}\right)_x = -B\cos(\omega t - \phi) \cdot (\nabla \phi)_z \quad (10)$$

[Formula 11]

$$|(\nabla \phi)_z| \gg \frac{1}{B}|(\nabla B)_z| \quad (11)$$

Likewise, formulae (12) and (13) can be obtained.

[Formula 12]

$$(rot\vec{B})_y = \left(\frac{\partial \vec{B}}{\partial z}\right)_y = B\sin(\omega t - \phi) \cdot (\nabla \phi)_z \quad (12)$$

[Formula 13]

$$(rot\vec{B})_y = \left(\frac{\partial \vec{B}}{\partial z}\right)_x + \left(\frac{\partial \vec{B}}{\partial z}\right)_y = -B\cos(\omega t - \phi) \cdot (\nabla \phi)_y + B\sin(\omega t - \phi) \cdot (\nabla \phi)_x \quad (13)$$

Based on the formulae (10), (12), and (13), the formula (3) can be converted to the formula (14) with a time average.

[formula 14]

$$SAR \propto |(\nabla \phi)_z|^2 + 0.5 \cdot [|(\nabla \phi)_x|^2 + |(\nabla \phi)_y|^2] \quad (14)$$

That is, it can be derived that the heat generation quantity SAR per a unit mass in the target object is proportional to a result obtained by adding a sum $[|(\nabla \phi)_x|^2 + |(\nabla \phi)_y|^2]$ of $|(\nabla \phi)_x|^2$ that is a square of a change level $|(\nabla \phi)_x|$ of the phase $\phi$ of the MR signal in the x direction and $|(\nabla \phi)_y|^2$ that is a square of a change level $|(\nabla \phi)_y|$ in the y direction, and, $|(\nabla \phi)_z|^2$ that is a square of a change level $|(\nabla \phi)_z|$ in the z direction at a rate of substantially 1:2.

As explained above, the phase information of the MR signal is a suitable barometer to predict the heat generation quantity SAR due to an eddy current. Hence, the image creating device 100 of this embodiment creates an image of predicting at which location the heat generation quantity SAR becomes remarkable using the phase information of the MR signal.

Figure 6:
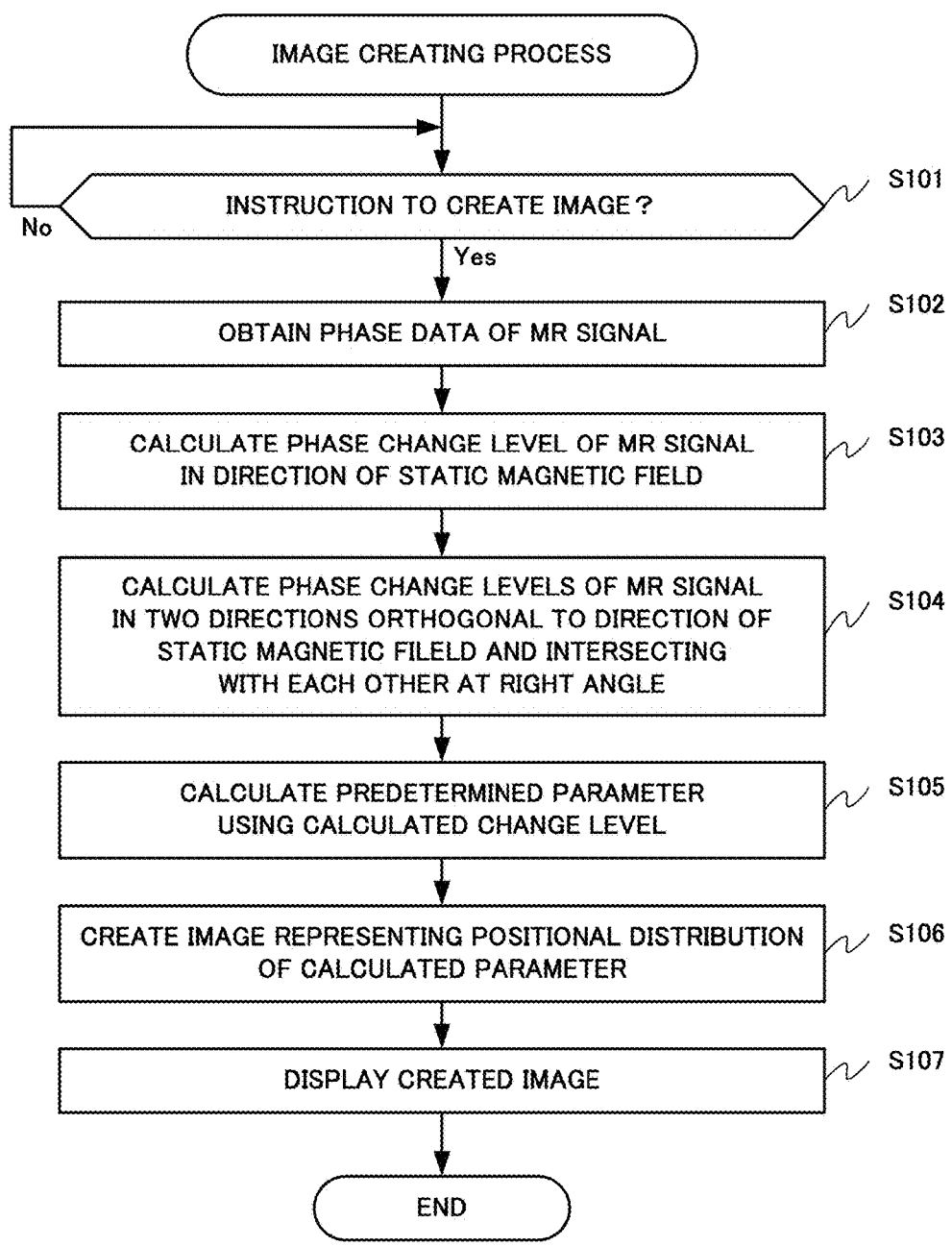
FIG. 6 is a flowchart illustrating an example operation of an image creating process.

FIG. 6 is a flowchart illustrating an example image creating process executed by the image creating device 100 of this embodiment.

In this flowchart, an explanation will be given of a process of creating an image in the zx plane of the phase information of the MR signal, that is, an image of the target object as viewed from the top. However, the image created by the image creating device 100 is not limited to an image on the zx plane, and may be an image on the yz plane, or may be an image on the xy plane, or an image of a cut plane cut along a plane not parallel with any of those three planes. Alternatively, the image creating device 100 may create a three-dimensional image representing the entire image-capture area including the target object.

When the process starts, first, the controller 110 of the image creating device 100 determines whether or not there is an image creation instruction (step S101). That is, the controller 110 determines whether or not the operator operates the operating device 140 and enters an instruction to create a phase image of the MR signal.

When it is determined that no image creation instruction has been made (step S101: No), the process remains at the step S101. That is, the controller 110 determines whether or not an image creation instruction is made and stands by until an image creation instruction is made.

Conversely, when it is determined that an image creating instruction is made (step S101: Yes), the controller 110 obtains the phase data of the MR signal (step S102). That is, the controller 110 obtains phase data from MR signal data obtained upon application of a static magnetic field and a high-frequency magnetic field to the target object in the MRI device 200. The phase data is, for example, divided into a sine signal and a cosine signal, that is, as to the MR signal detected as complex data containing a real component and an imaginary component, the phase data is obtained by taking a reverse tangent of the ratio between the real component data and the imaginary component data.

The image creating process of this embodiment is suitably executed before a high-frequency magnetic field with a high intensity is applied to the target object to start a full image-capture. The intensity of the high-frequency magnetic field applied to the target object to obtain phase data is desirably lower than the intensity of the high-frequency magnetic field to be applied to the target object during the time period of magnetic resonance image-capture. When, however, the intensity is too low, due to an adverse effect of noises and the like, a precise measurement becomes difficult. Hence, it is desirable that the intensity of the high-frequency magnetic field applied to the target object to obtain phase data should be approximately 1/20 to 1/250 of the intensity of the high-frequency magnetic field to be applied to the target object during the time period of magnetic resonance image-capture.

In this case, the MR signal has data at a position resolution in a voxel unit when a magnetic field is applied in the MRI device 200. The controller 110 may obtain the phase data for all voxels, or may obtain the phase data for necessary voxels only. For example, the controller 110 may obtain the phase data for the zx plane to be imaged and respective voxels therearound. In addition, in order to improve the process efficiency, the controller 110 may obtain the phase data for a unit of several voxels collected.

When the phase data of the MR signal is obtained, the controller 110 calculates a change level $(\nabla \phi)_z$ in the static magnetic field direction (z direction) of the phase of the MR signal at each obtained position (step S103). That is, the controller 110 obtains for respective pieces of phase data obtained in the unit of voxel, a difference of the phase value with a voxel adjoining in the z direction, and calculates a value divided by a distance between the voxels at which the difference is obtained. At this time, data of multiple voxels adjoining in the z direction may be subjected to smoothing, and $(\nabla\phi)_z$ may be calculated.

Still further, the controller 110 calculates change levels $(\nabla\phi)_x$ and $(\nabla\phi)_y$ of the phase of the MR signal in the two directions orthogonal to the static magnetic field direction and intersecting with each other at right angle (step S104). That is, like the z direction, the controller 110 obtains, for respective pieces of phase data obtained in the unit of voxel, a difference of the phase value with the voxels adjoining in the x direction and the y direction, and calculates a value divided by a distance between the voxels through which the difference is obtained.

When the phase change level is calculated, the controller 110 calculates a predetermined parameter for image display using the calculated change level (step S105). More specifically, as indicated in the following formula (15), the controller 110 calculates, for each voxel calculated in the step S103 and the step S104, a parameter that is an addition of the square of the change level in the z direction and the sum of the squares of the change levels in the x direction and y direction at a rate of 1:2.

[Formula 15]

$$|(\nabla\phi)_z|^2 + 0.5\cdot|(\nabla\phi)_x + (\nabla\phi)_y|^2 \qquad (15)$$

When the parameter for image display is calculated, the controller 110 creates an image representing the positional distribution of the calculated parameters (step S106), and displays the created image (step S107). That is, the controller 110 creates, for the parameter expressed by the formula (15), an image representing the planar distribution in the zx plane, and displays the created image on the display 130 at a predetermined synchronous timing. When, for example, the image creating device 100 creates a three-dimensional image of the image-capture area including the target object, the controller 110 creates an image representing a spatial distribution of the parameter expressed by the formula (15).

When the created image is displayed, the process through this flowchart ends.

According to such a configuration, the image creating device 100 of this embodiment calculates, for the phase of the MR signal, a change level in the static magnetic field direction and a sum of change levels in the two directions orthogonal to each other and perpendicular to the static magnetic field, and creates an image representing the positional distribution of parameters obtained by an addition of the squares of both calculation results at a rate of 2:1. As a result, a predicted distribution of heat generation quantities due to an application of the high-frequency magnetic field can be obtained without applying a highly intensive high-frequency magnetic field.

Next, an explanation will be given of two test results carried out to check predicted distribution of heat generation SAR by the aforementioned image creating device 100.

The first test was carried out for the purpose of comparing the predicted distribution of SAR created through the method according to the aforementioned embodiment and a distribution of SAR created through a conventional scheme.

As a phantom subjected to a measurement, a columnar bottle (7×7×11.3 cm³: polyester ointment bottle, made by AS ONE Corporation) filled with a solution of potassium chloride at a concentration of 1.5% which has an equal electrical conductivity to the cerebral fluid of human was prepared. As the MRI device, 1.5-tesla MRI device (SIGNA Horizon LX, GE Health Care Japan Corporation) was utilized. In addition, using a transmitter/receiver head coil, the phantom was disposed vertically, that is, disposed so that the center axis of the cylindrical bottle was directed in the vertical direction (y direction).

An SPGR (Spoiled Gradient Echo) technique was applied as an image-capture method, and an image of the phantom was captured with a single slice having a slice thickness of 5 mm. In addition, an interval (TR: Repetition Time) of applying RF pulses was set to be 100 ms, and the echo time (TE: Echo Time) was set to be 10 ms. The image-capture area (FOV: Field of View) was set to be 240 mm×240 mm, the matrix size was set to be 256×256, and the number of adding signals was set to be 1.

Under such a condition, a high-frequency magnetic field having an intensity that causes the FA to be 10 degrees was applied to the phantom as a high-frequency magnetic field with a lower intensity than those of typical high-frequency magnetic fields to be applied to a target object during the time period of image-capture in the MRI. Next, the MR signal from the phantom was detected as complex data containing a real component and an imaginary component, and the phase of the MR signal was obtained upon taking a reverse tangent of the ratio between the real data and the imaginary data. Subsequently, the change level $(\nabla\phi)_z$ of the phase of the obtained MR signal in the z direction and the change level $(\nabla\phi)_x$ in the x direction were obtained, and a value $[(\nabla\phi)_z]^2 + 0.5\cdot[(\nabla\phi)_x]^2$ that is an addition of the respective squares of the obtained change levels at a rate of 2:1 was calculated. A distribution obtained by dividing each calculated value $[(\nabla\phi)_z]^2 + 0.5\cdot[(\nabla\phi)_x]^2$ by the maximum value was obtained. Since the phase change level in the y direction center of the phantom was calculated, the phase change level $(\nabla\phi)_y$ in the y direction that was a small value was not taken into consideration.

Figure 7A:
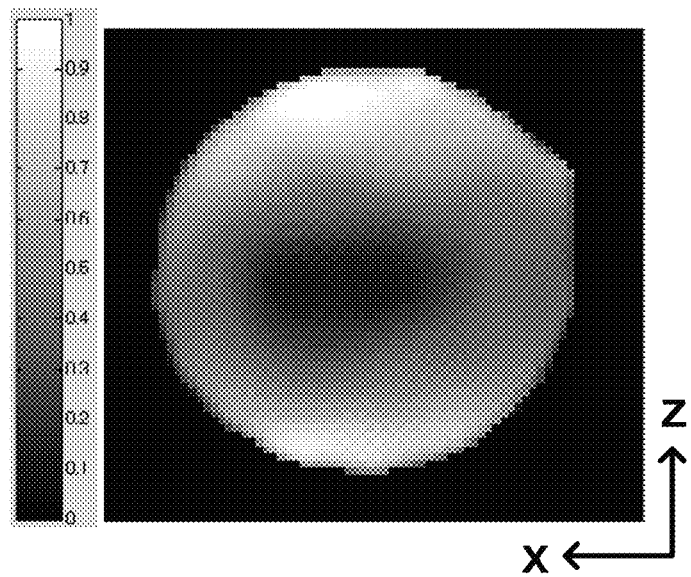
FIG. 7A is a diagram illustrating a predicted distribution of heat generation quantities created through a method of the present disclosure.

As a result, an image representing the positional distribution of $[(\nabla\phi)_z]^2 + 0.5\cdot[(\nabla\phi)_x]^2$ illustrated in FIG. 7A was obtained. The obtained distribution of $[(\nabla\phi)_z]^2 + 0.5\cdot[(\nabla\phi)_x]^2$ was mainly dependent on the z direction (static magnetic field direction), and indicated a higher value around the marginal portion of the phantom.

Figure 7B:
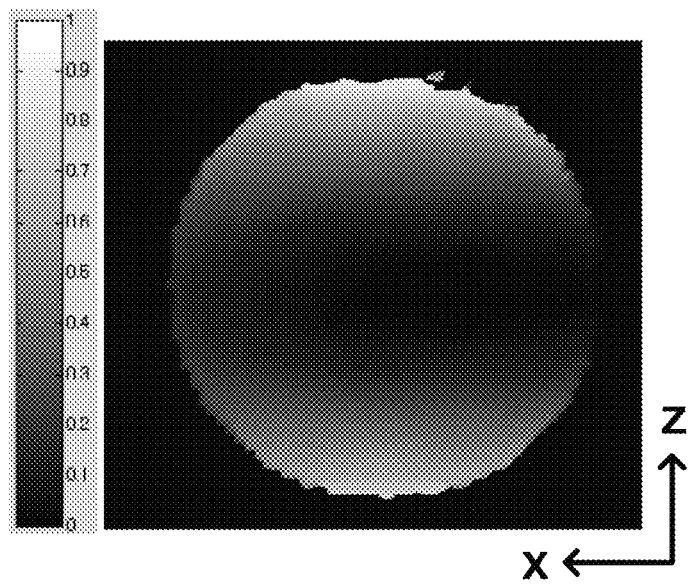
FIG. 7B is a diagram illustrating a distribution of heat generation quantities created through a conventional method.

Conversely, FIG. 7B illustrates the positional distribution of SAR created through the technique disclosed in the aforementioned Non-patent Literature 1. When the distribution in FIG. 7A is compared with the distribution of SAR in FIG. 7B, both distributions were mainly dependent on the z direction, and indicated a higher value around the marginal portion of the phantom. In order to obtain the distribution in FIG. 7B through the conventional technology, it is necessary to apply a highly intensive high-frequency magnetic field to a target object, and thus there is a possibility that a remarkable heat generation is caused in practice.

According to the aforementioned first test, it was confirmed that the positional distribution of SAR like that of the conventional technology can be obtained upon application of a high-frequency magnetic field with a low intensity through the method of this embodiment utilizing the phase information.

The second test was carried out for the purpose of checking whether or not the predicted map of SAR created with an application of a high-frequency magnetic field with a low intensity predicts a location that actually generates heat under application of a highly intensive high-frequency magnetic field.

Figure 8A:
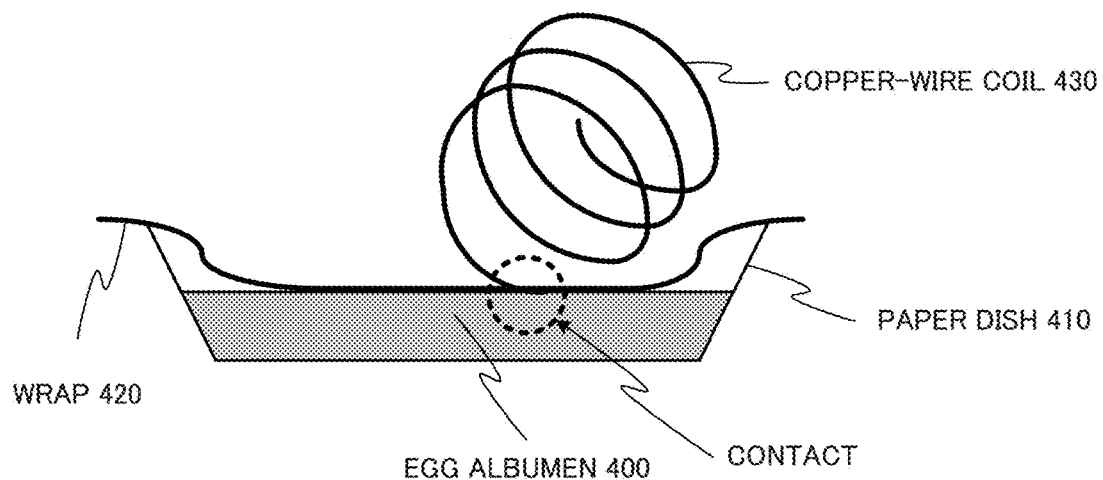
FIG. 8A is a diagram illustrating an outline of a measurement target used in a test.
Figure 8B:
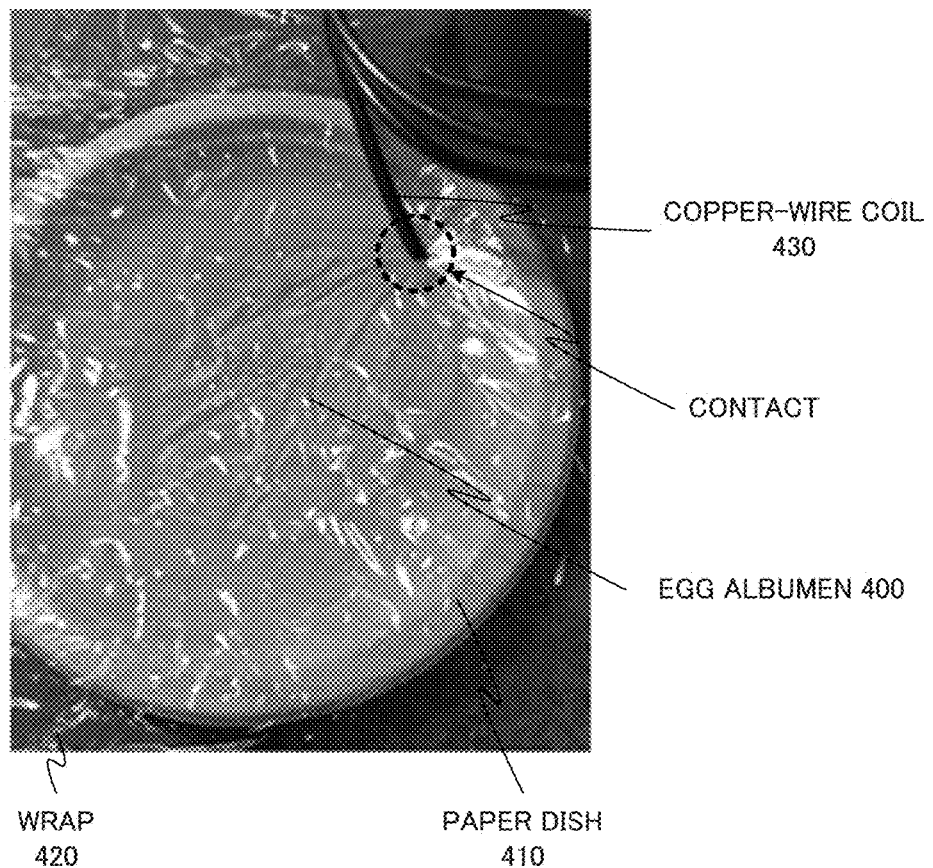
FIG. 8B is a diagram illustrating a processed photograph of the measurement target used in the test.

First, the test started with a selection of a phantom to be a measurement target. In consideration of an easiness of checking of the presence/absence of heat generation when a highly intensive high-frequency magnetic field is applied through thermal denaturation, egg albumen was selected as a phantom. More specifically, as illustrated in FIG. 8A, and egg albumen 400 was put in a paper dish 410, and the egg albumen 400 was covered with a transparent wrap 420 (NEW Krewrap, made by KUREHA CORPORATION) from the upper space. Next, in order to generate an eddy current, a copper-wire coil 430 having a copper wire with a thickness of 5 mm wound substantially three times in a loop shape (diameter of loop: substantially 15 cm) was prepared, and the leading end of the copper-wire coil 430 was caused to contact the egg albumen 400 via the wrap 420 so as to be put therein. FIG. 8B is a diagram of a processed photograph showing the egg albumen 400, the copper-wire coil 430, and the like disposed in practice under the aforementioned condition.

In this case, the reason why the leading end of the copper-wire coil 430 was disposed so as to contact the wrap 420 is as follows.

First, in order to efficiently generate an eddy current in the system of FIG. 8A that is a phantom including the looped copper-wire coil 430 and the egg albumen 400, it is important to cause this system to resonate with a resonant frequency ω of the MRI device. As to the resonance condition, when the inductance of this system mainly including the copper-wire coil 430 is L, and the capacitance is C, $\omega = 1/\sqrt{(L \times C)}$ is satisfied. Hence, in order to let the system of FIG. 8A resonated, the presence of an appropriate capacitance is necessary. In consideration of such a need, in this test, the copper-wire coil 430 was caused to contact the egg albumen 400 via the wrap 420 so as to have a gap by what corresponds to the thickness of the wrap 420 between the copper-wire coil 430 and the egg albumen 400.

Second, when the contact resistance between the copper-wire coil 430 and the egg albumen 400 is r, and the eddy current flowing through the copper-wire coil 430 is i, the power consumption at the contact portion between the copper-wire coil 430 and the egg albumen 400 is proportional to $r \times i \times i$. Hence, the greater the contact resistance r is, the more the heat generation quantity increases. The smaller the contact area is, the greater the contact resistance r becomes. Hence, the smaller the contact area is, the greater the heat generation quantity becomes. In consideration of this fact, in this test, the leading end of the copper-wire coil 430 was caused to contact the egg albumen 400 via the wrap 420 so as to make the contact area as small as possible.

That is, when a highly conductive metal coil like the copper-wire coil 430 and a substance with a thermal denaturation property like the egg albumen 400 were appropriately spaced apart from each other by an insulator like the wrap 420, and were caused to contact with each other with a small contact area, and thus a phantom which efficiently generates heat by an eddy current was prepared.

In order to carry out a test using such a phantom including the egg albumen 400 and the copper-wire coil 430, and the like, as the MRI device, like the aforementioned first test, 1.5-tesla MRI device (SIGNA horizon LX, made by GE Health Care Japan Corporation) was utilized. In addition, an image of the phantom was captured using a transmitter/receiver body coil.

As the imaging method, the SPGR technique was applied, and an image of the target object was captured using a single slice having a slice thickness of 10 mm. In addition, the interval (TR) of applying RF pulses was set to be 18 ms, the echo time (TE) was set to be 10 ms, the image-capture area (FOV) was set to be 480 mm×480 mm, the matrix size was set to be 256×256, and the number of signal applications was set to be 26 so as to make the scanning time substantially two minutes.

Under such a condition, a high-frequency magnetic field with a low intensity causing the FA to be around 10 degrees was applied to the phantom. At this time, since the intensity of the applied high-frequency magnetic field was low, the thermal denaturation of the egg albumen 400 was not observed.

Conversely, the distribution of the change level $(\nabla \phi)_z$ in the z direction of the phase of the MR signal was obtained. More specifically, the MR signal from the phantom was detected as complex data containing a real component and an imaginary component, and the phase of the MR signal was obtained by taking the reverse tangent of the ratio between the real data and the imaginary data. Next, the change level $(\nabla \phi)_z$ in the z direction of the obtained phase of the MR signal was obtained, the square $[(\nabla \phi)_z]^2$ of the obtained change level was calculated, and a distribution of values obtained by dividing the respective calculated squares $[(\nabla \phi)_z]^2$ of the change levels by the maximum value therein was obtained. In the second test, in order to simplify the process, it was presumed that the phase change level in the x direction and the y direction is small relative to the phase change level in the z direction, the phase change level in the x direction and the y direction was not calculated, and only the phase change level in the z direction was calculated.

Figure 9A:
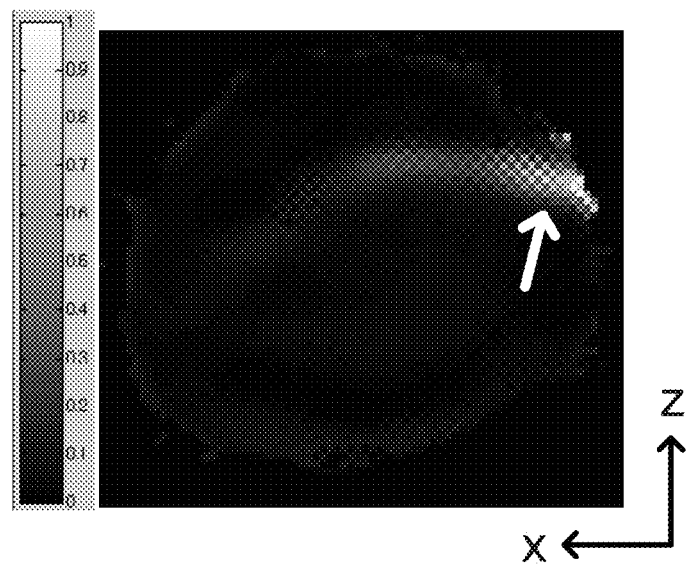
FIG. 9A is a diagram illustrating a predicted distribution of heat generation quantities created under a condition in which a high-frequency magnetic field with a low intensity has been applied.

As a result, as illustrated in FIG. 9A, an image representing the positional distribution of $[(\nabla \phi)_z]^2$ was obtained. In the obtained image, the value around the position where the leading end of the copper-wire coil 430 contacted (a portion indicated by an arrow in the figure) was particularly high.

Figure 9B:
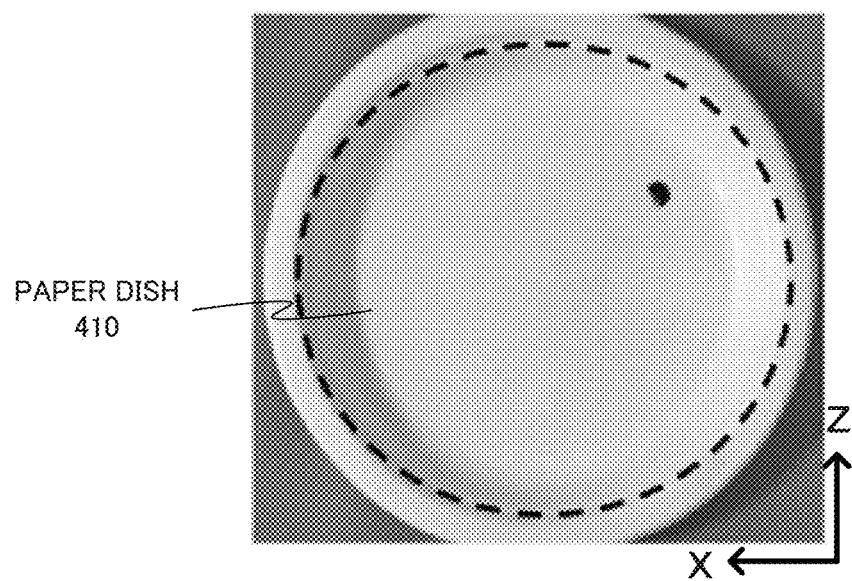
FIG. 9B is a diagram illustrating the condition of a phantom generating heat under the application of the high-frequency magnetic field with a high intensity.

In addition, a high-frequency magnetic field with a high intensity causing the FA to be 90 degrees was also applied to the same phantom disposed in the same way. As a result, the egg albumen 400 caused a thermal denaturation, and as illustrated in FIG. 9B, a part of the container that was the paper dish 410 was burnt. The burnt position substantially matched the position where the value of $[(\nabla \phi)_z]^2$ was large in FIG. 9A. In FIG. 9B, the dotted line near the edge of the container indicates the contour of the solution that was the egg albumen 400.

According to the aforementioned second test, it was confirmed that, through the method utilizing the phase change level in the static magnetic field direction of the MR signal, the distribution of SAR is effectively predictable as a preliminary image-capture before an actual image-capture is performed while applying a highly intensive high-frequency magnetic field to a target object.

The present disclosure is not limited to the aforementioned embodiment, and permits various modifications and changes. The aforementioned embodiment is to explain the present disclosure, and is not to limit the scope of the present disclosure.

For example, in the aforementioned embodiment, image information representing the positional distribution of parameters depending on the change level $(\nabla \phi)_z$ of the phase φ of the magnetic resonance signal (MR signal) in the direction of the static magnetic field $B_0$ per a predetermined distance which is generated from a target object upon application of the static magnetic field $B_0$ and the high-frequency magnetic field $B_1$ serving as barometers indicating a heat generation quantity is created, and such image information is displayed as an example. However, the information representing the positional distribution of parameters depending on the change level $(\nabla \phi)_z$ is not limited in the form of image information. For example, it may be a list including a pair of a positional coordinate and a value, that is, in the form of a table. In addition, how to express such information visually to the user is optional.

For example, in the aforementioned embodiment, the image creating device 100 calculates, for the phase of the MR signal, a change level in the z direction and a sum of change levels in the x direction and the y direction, adds the respective squares at a ratio of 2:1 to obtain a parameter, and creates an image of such a parameter. However, the parameter for imaging in the present disclosure is not limited to this example. For example, the direction in which the phase change level is calculated is not limited to the x direction and the y direction, and may be any two directions orthogonal to the z direction (static magnetic field direction) and intersecting with each other at right angle. For example, the phase change level in two directions inclined by 45 degrees from the x direction and the y direction, respectively, in the same direction may be calculated. In addition, in order to reduce an amount of calculation, the image creating device 100 may create an image of parameters that are a phase change level $(\nabla\phi)_z$ in the z direction and the square $[(\nabla\phi)_z]^2$ thereof without utilizing the phase change level $(\nabla\phi)_x$ in the x direction and the phase change level $(\nabla\phi)_y$ in the y direction. Oppositely, the image creating device 100 may create an image of parameters that are the phase change level $(\nabla\phi)_x$ in the x direction and the square $[(\nabla\phi)_x]^2$ thereof, or the phase change level $(\nabla\phi)_y$ in the y direction and the square $[(\nabla\phi)_y]^2$ thereof without utilizing the phase change level $(\nabla\phi)_z$ in the z direction. That is, a parameter depending on any of $(\nabla\phi)_z$, $(\nabla\phi)_x$, and $(\nabla\phi)_y$ can be utilized as a parameter for an image representing the predicted distribution of the SAR.

Moreover, the image creating device 100 of the present disclosure may create multiple images of the phase information of the MR signal explained above for different planes. That is, the image creating device may create images representing the way cut along the zx plane for two locations having different heights, or may create multiple images for any different planes like the xy plane and the zx plane. By creating multiple images, the image creating device 100 of the present disclosure can provide information on a location where a high SAR is predicted more precisely.

Figure 10:
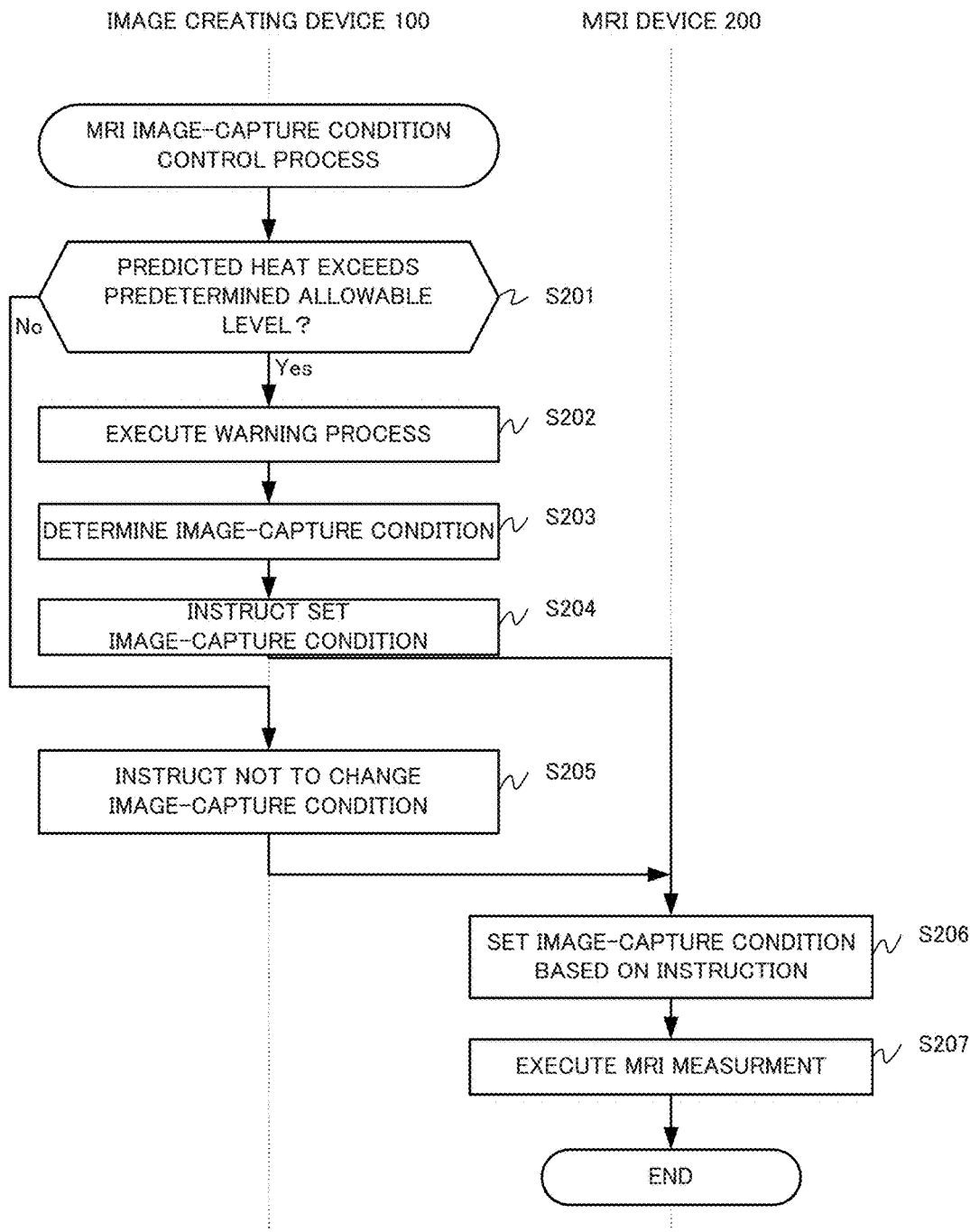
FIG. 10 is a flowchart illustrating an example process of controlling an image-capture condition of an MRI.

Alternatively, the image creating device 100 of the present disclosure may create an image representing the predicted distribution of to-be generated heat, and then execute a process of controlling the image-capture condition of the MRI device 200 illustrated in the flowchart of FIG. 10.

In the flowchart of FIG. 10, the controller 110 of the image creating device 100 determines whether or not an amount of to-be generated heat predicted based on the imaged positional distribution exceeds a predetermined allowable level (step S201). In this case, the predicted heat generation quantity is a quantity obtained from the phase change level of the MR pulses, the intensity of the magnetic field, and the like as indicated in the formula (12). The controller 110 obtains the predicted heat generation quantity, and compares this value with the predetermined allowable level, thereby determining whether or not there is a possibility of heat generation.

The predicted heat generation quantity for the determination may be obtained from, for example, a sum of predicted heat generation quantities for all captured imaged depicting positional distributions. Alternatively, it is expected that the locations where the predicted heat generation quantities increase are concentrated within a certain narrow range as illustrated in FIG. 9A, and thus the predicted heat generation quantity may be obtained from a sum of the predicted heat generation quantities within a certain range where the value is relatively higher than other ranges.

When it is determined in the step S201 that the predicted heat generation quantity exceeds the predetermined allowable level (step S201: Yes), the controller 110 executes a warning process (step S202). For example, the controller 110 displays warning text and images on the display 130 together with the created predicted image for heat generation. Alternatively, a warning sound may be output.

Upon execution of the warning process, the controller 110 sets the image-capture condition to be set during the time period of magnetic resonance image-capture on a target object so as to prevent the predicted heat generation quantity from exceeding the allowable level (step S203), and sends the set image-capture condition to the MRI device 200 (step S204). That is, in order to prevent the heat generation in the target object, and to reduce the heat generation quantity as much as possible, the controller 110 transmits an instruction and an order to the MRI device 200 through, for example, the communicator 150 so as to change the image-capture condition of the MRI measurement being performed on the target object.

This will be explained with a more specific example, and when determining that the predicted heat generation quantity exceeds the predetermined allowable level, the controller 110 decreases a duty cycle D that is a time rate of applying RF pulses in a pulse sequence, or decreases the number of multi slices. At this time, it is preferable that the higher the rate of the predicted heat generation quantity exceeding the predetermined allowable level is, the more the controller 110 decreases the duty cycle D or decreases the number of multi slices. In addition, when the predicted heat generation quantity exceeds an allowable level limit, the controller 110 may decide to terminate an MRI image-capture to be performed on the target object.

Conversely, when it is determined in the step S201 that the predicted heat generation quantity does not exceed the predetermined allowable level (step S201: No), the controller 110 instructs the MRI device 200 not to change the image-capture condition set during the time period of magnetic resonance image-capture on the target object (step S205).

When the instruction is given to the MRI device 200, the MRI device 200 sets the image-capture condition based on the instruction from the image creating device 100 (step S206), and performs MRI measurement (step S207). Subsequently, this flowchart ends. As explained above, when a heat generation is predicted, the image-capture condition of the MRI measurement to be performed on the target object is changed so as to decrease the heat generation quantity, thereby preventing heat generation and reducing the heat generation quantity in the MRI measurement.

In the aforementioned embodiment, the explanation was given of a case in which the program executed by the CPU is stored in the ROM or the memory in advance, but the present disclosure is not limited to this case, and the program for executing the aforementioned processes may be applied to a conventional general-purpose computer to allow such a computer to function as the image creating device 100 of the aforementioned embodiment.

How to provide such a program is optional, and for example, the program may be stored in a computer-readable non-transitory memory medium (for example, a flexible disc, a CD (Compact Disc)-ROM, a DVD (Digital Versatile Disc)-ROM), and such a memory medium may be distributed, or the program may be stored in a storage over a network like the Internet, and may be downloaded and provided.

When the above-explained processes are realized by shared works of an OS and an application program or are realized by a cooperative work of the OS and the application program, only the application program portion may be stored in a memory medium or a storage. In addition, the program may be superimposed on carrier waves and distributed through a network. For example, the program may be posted on a bulletin board (BBS: Bulletin Board System) over a network, and the program may be distributed through the network. Next, a configuration in which, this program is launched and executed under the control of the OS likewise other application programs so that the execution of the above-explained processes are enabled, may be employed.

The present disclosure can permit various embodiments and modifications without departing from the scope of the present disclosure. The aforementioned embodiment is to explain the present disclosure, and is not to limit the scope of the present disclosure.

This application is based on Japanese Patent Application No. 2012-080885 filed on Mar. 30, 2012. The whole specification, claims and drawings of Japanese Patent Application No. 2012-080885 are herein incorporated in this specification by reference.

INDUSTRIAL APPLICABILITY

The present disclosure is widely applicable to a device and a method that predict a heat generation quantity inherent to an application of a high-frequency magnetic field.

REFERENCE SIGNS LIST

100 Image creating device
110 Controller
120 Memory
130 Display
140 Operating device
150 Communicator
200 MRI device
210 Gantry
211 Static magnetic field magnet
212 Gradient magnetic field coil
213 Transmitter coil
214 Receiver coil
220 Static magnetic field control device
230 Gradient magnetic field control device
240 High-frequency transmitter
250 High-frequency receiver
300 Living body
400 Egg albumen
410 Paper dish
420 Wrap
430 Copper-wire coil

The invention claimed is:

1. A magnetic resonance imaging device that generates information representing a heat generation distribution, the device comprising:
an obtaining unit configured to use a computer to obtain a phase of a magnetic resonance signal generated from a target object upon application of a static magnetic field and a high-frequency magnetic field to the target object;
a calculating unit configured to use a computer to calculate a change level of the obtained phase per a predetermined distance in a direction of the static magnetic field; and
a generating unit configured to use a computer to generate an image representing a positional distribution of a parameter depending on the calculated change level, wherein the image predicts the heat generation distribution in the target object.

2. The device according to claim 1, wherein the parameter is proportional to a square of the calculated change level.

3. The device according to claim 1, wherein:
The calculating unit calculates a change level of the obtained phase per a predetermined distance in a direction orthogonal to the direction of the static magnetic field; and
The generating unit generates the image representing a positional distribution of a parameter, the parameter being obtained by an addition of a square of the calculated change level in the direction of the static magnetic field and a square of the calculated change level in the orthogonal direction to the direction of the static magnetic field at a predetermined ratio.

4. The device according to claim 1, wherein:
the calculating unit calculates change levels of the obtained phase per a predetermined distance in two directions orthogonal to the direction of the static magnetic field and intersecting with each other at right angle; and
the generating unit creates an image representing a positional distribution of a parameter, the parameter being obtained by an addition of a square of the calculated change level in the direction of the static magnetic field, and, a square of a sum of the calculated change levels in the two directions orthogonal to the direction of the static magnetic field and intersecting with each other at right angle at a rate of substantially 2:1.

5. The device according to claim 1, wherein an intensity of the high-frequency magnetic field is lower than an intensity of a high-frequency magnetic field to be applied to the target object during a time period of magnetic resonance image-capture being performed on the target object.

6. The device according to claim 5, wherein the intensity of the high-frequency magnetic field is lower than 1/20 of the intensity of the high-frequency magnetic field to be applied to the target object during the time period of magnetic resonance image-capture being performed on the target object.

7. The device according to claim 1, further comprising an image creator that creates an image representing the amount of heat that is predicted to be generated based on the positional distribution of the parameter.

8. The device according to claim 1, further comprising a warner that outputs a warning when quantity of heat to be generated that is predicted based on the positional distribution exceeds a predetermined allowable level.

9. The device according to claim 1, further comprising a setter that determines an image-capture condition to be set during a time period of magnetic resonance image-capture being performed on the target object so as to prevent, when a heat generation quantity predicted based on the positional distribution exceeds a predetermined allowable level, the heat generation quantity from exceeding the allowable level.

10. A magnetic resonance imaging method comprising:
an obtaining step comprising a computer configured for obtaining a phase of a magnetic resonance signal generated from a target object upon application of a static magnetic field and a high-frequency magnetic field to the target object;

a calculating step comprising a computer configured for calculating a change level of the obtained phase per a predetermined distance in a direction of the static magnetic field; and a generating step comprising a computer configured for generating an image representing a parameter depending on the calculated change level, wherein the image predicts the heat generation distribution in the target object.

11. A non-transitory computer-readable recording medium storing a program that causes a computer in a magnetic resonance imaging device to function as:

an obtaining unit comprising a computer configured for obtaining a phase of a magnetic resonance signal generated from a target object upon application of a static magnetic field and a high-frequency magnetic field to the target object;

a calculating unit comprising a computer configured for calculating a change level of the obtained phase per a predetermined distance in a direction of the static magnetic field; and a generating unit comprising a computer configured for generating an image representing a parameter depending on the calculated change level, wherein the image predicts the heat generation distribution in the target object.

* * * * *